United States Patent
Scott et al.

(10) Patent No.: US 7,210,814 B2
(45) Date of Patent: May 1, 2007

(54) DENTAL CURING LIGHT WITH SPECIALLY ARRANGED LEDS

(75) Inventors: Robert R. Scott, Riverton, UT (US);
Dee Jessop, West Jordan, UT (US);
Dan E. Fischer, Sandy, UT (US)

(73) Assignee: Ultradent Products, Inc., South Jordan, UT (US)

( * ) Notice: Subject to any disclaimer, the term of this patent is extended or adjusted under 35 U.S.C. 154(b) by 110 days.

(21) Appl. No.: 11/118,147

(22) Filed: Apr. 29, 2005

(65) Prior Publication Data
US 2006/0245187 A1    Nov. 2, 2006

(51) Int. Cl.
*F21V 9/00*    (2006.01)
(52) U.S. Cl. ............... 362/231; 362/234; 362/804; 433/29; 600/249
(58) Field of Classification Search ......... 362/119, 362/230, 804, 231, 234; 433/29; 250/504 H; 606/13; 600/241, 245, 249
See application file for complete search history.

(56) References Cited

U.S. PATENT DOCUMENTS

| | | | |
|---|---|---|---|
| 5,420,768 A | 5/1995 | Kennedy | 362/119 |
| 6,102,696 A | 8/2000 | Osterwalder et al. | 433/29 |
| 6,200,124 B1 | 3/2001 | Buazza et al. | 425/174.4 |
| 6,200,134 B1 * | 3/2001 | Kovac et al. | 433/29 |
| 6,331,111 B1 | 12/2001 | Cao | 433/29 |
| 6,465,961 B1 | 10/2002 | Cao | 315/58 |
| 6,498,108 B2 | 12/2002 | Cao | 438/706 |
| 6,514,975 B1 * | 2/2003 | Maw | 514/252.19 |
| 6,607,384 B1 | 8/2003 | Nakanishi | 433/29 |
| 6,634,770 B2 | 10/2003 | Cao | 362/294 |
| 6,634,771 B2 | 10/2003 | Cao | 362/294 |
| 6,700,158 B1 | 3/2004 | Cao | 257/330 |
| 6,719,446 B2 | 4/2004 | Cao | 362/547 |
| 6,719,558 B2 | 4/2004 | Cao | 433/29 |
| 6,746,885 B2 | 6/2004 | Cao | 438/26 |

(Continued)

FOREIGN PATENT DOCUMENTS

CA    02387665    12/2002

(Continued)

OTHER PUBLICATIONS

Spectral Analysis of Commercial LED Dental Curing Lights, G. R. Parr, et al. URL: http://www.iadr.confex.com/iadr/2002SanDiego/techprogram/abstract-19567.htm.

*Primary Examiner*—John Anthony Ward
(74) *Attorney, Agent, or Firm*—Workman Nydegger

(57) ABSTRACT

A dental curing light including an elongate wand having a proximal end and a distal end, a plurality of LEDs disposed at or near a distal end of the elongate wand and a printed circuit board for mounting the plurality of LEDs. The LEDs include a main through mount LED and a plurality of surface mount LEDs positioned around the main through mount LED. The main LED is through mounted relative to the printed circuit board such that the power connections of the main through mount LED are made through a hole or holes in the printed circuit board. The power connections of the main through mount LED are made on an opposite surface of the printed circuit board relative to the "top" surface to which the surface mount LEDs are mounted.

29 Claims, 6 Drawing Sheets

U.S. PATENT DOCUMENTS

| | | | |
|---|---|---|---|
| 6,755,647 B2 | 6/2004 | Melikechi et al. | 433/29 |
| 6,755,648 B2 | 6/2004 | Cao | 433/29 |
| 6,755,649 B2 | 6/2004 | Cao | 433/29 |
| 6,780,010 B2 | 8/2004 | Cao | 433/29 |
| 6,783,362 B2 | 8/2004 | Cao | 433/29 |
| 6,799,967 B2 | 10/2004 | Cao | 433/29 |
| 6,824,294 B2 | 11/2004 | Cao | 362/231 |
| 6,910,886 B2 * | 6/2005 | Cao | 433/29 |
| 6,926,524 B2 | 8/2005 | Cao | 433/29 |
| 6,929,472 B2 | 8/2005 | Cao | 433/29 |
| 6,981,867 B2 * | 1/2006 | Cao | 433/29 |
| 2001/0046652 A1 | 11/2001 | Ostler et al. | 433/29 |
| 2002/0177096 A1 | 11/2002 | Cao | 433/29 |
| 2002/0187454 A1 | 12/2002 | Melikechi et al. | 433/29 |
| 2003/0147258 A1 | 8/2003 | Fischer et al. | 362/573 |
| 2004/0004844 A1 | 1/2004 | Ryan, Jr. | 362/545 |
| 2004/0047662 A1 | 3/2004 | Ozawa et al. | 399/388 |
| 2004/0076921 A1 | 4/2004 | Gofman et al. | 433/29 |
| 2004/0120162 A1 | 6/2004 | Tsimerman et al. | 362/573 |
| 2004/0152038 A1 | 8/2004 | Kumagai et al. | 433/29 |

FOREIGN PATENT DOCUMENTS

| | | |
|---|---|---|
| EP | 1260192 | 11/2002 |
| JP | 1989/0328467 | 8/1991 |
| JP | 5-102525 | 4/1993 |
| JP | 2003/135485 | 5/2003 |
| WO | WO 99/16136 | 4/1999 |
| WO | WO 99/21505 | 5/1999 |
| WO | WO 01/19280 | 3/2001 |
| WO | WO 01/26576 | 4/2001 |

* cited by examiner

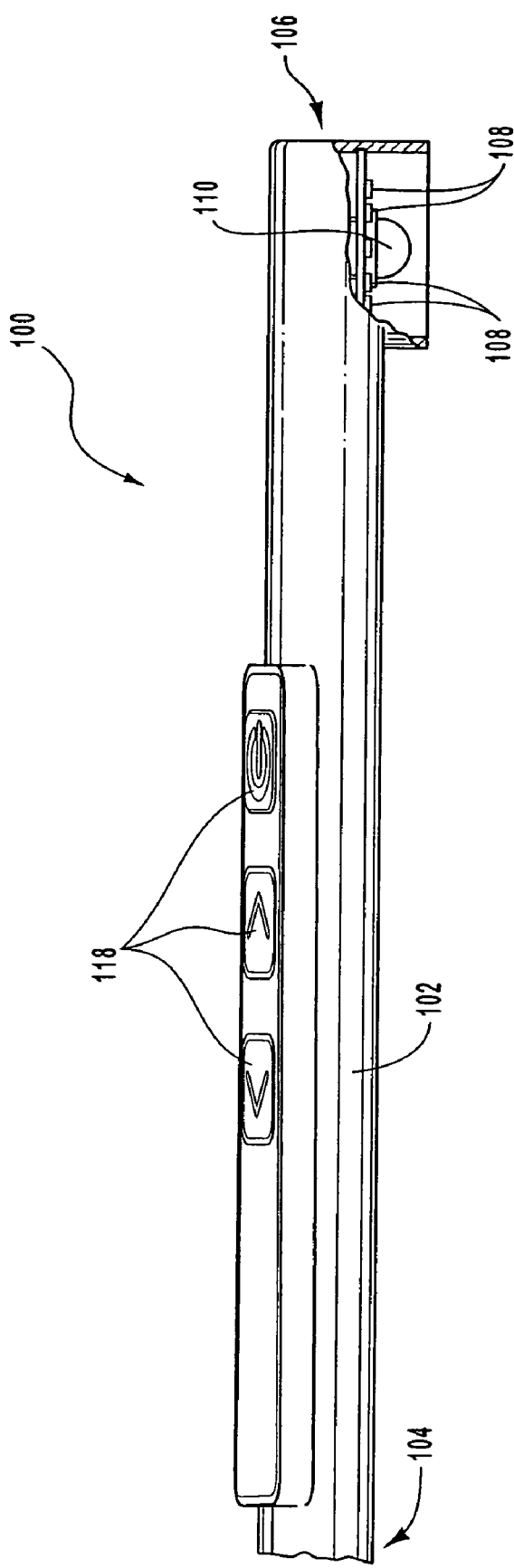

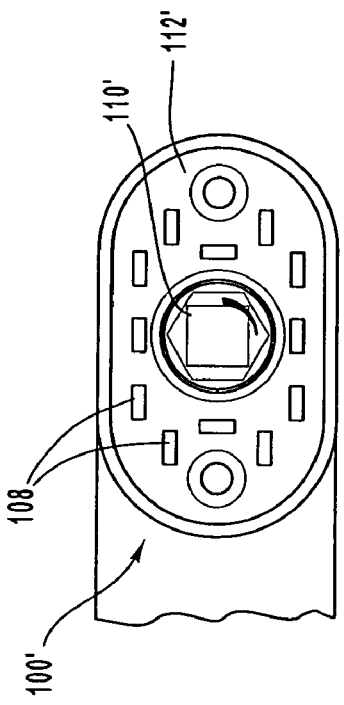
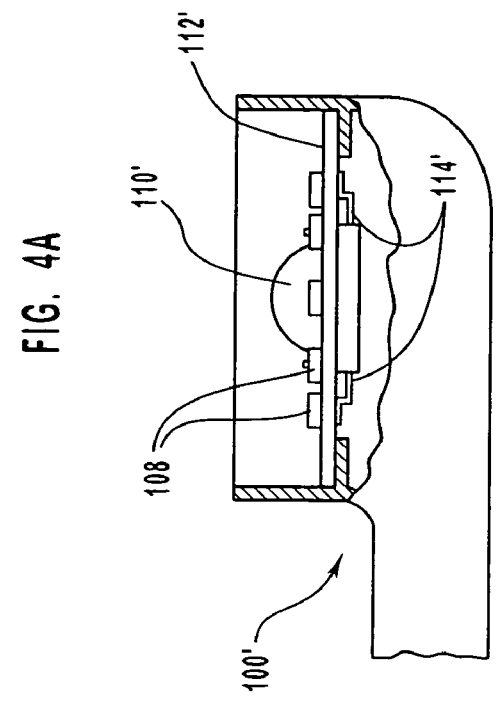
FIG. 3A
FIG. 4A
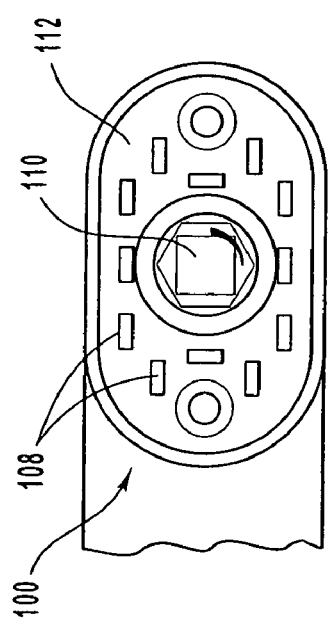
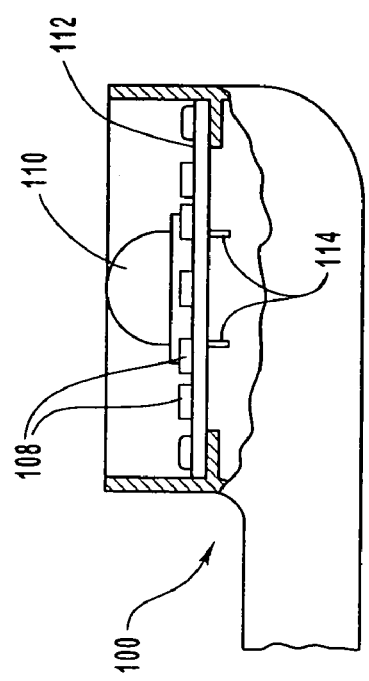
FIG. 3B
FIG. 4B

DENTAL CURING LIGHT WITH SPECIALLY ARRANGED LEDS

BACKGROUND OF THE INVENTION

1. The Field of the Invention

The present invention generally relates to the field of light curing devices and, more specifically, to light curing devices incorporating light emitting diodes (LEDs).

2. The Relevant Technology

In the field of dentistry, dental cavities are often filled and/or sealed with photosensitive compounds that are cured by exposure to radiant energy, such as visible light. These compounds, commonly referred to as light-curable compounds, are placed within dental cavity preparations or onto dental surfaces where they are subsequently irradiated by light. The radiated light causes photosensitive components within the compounds to polymerize, thereby hardening the light-curable compounds within the dental cavity preparation or another desired location.

Existing light-curing devices are typically configured with a light source, such as a quartz-tungsten-halogen (QTH) bulb or an LED light source. QTH bulbs are particularly useful because they are configured to generate a broad spectrum of light that can be used to cure a broad range of products. In particular, a QTH bulb is typically configured to emit a continuous spectrum of light in a preferred range of about 350 nm to about 500 nm. Some QTH bulbs may even emit a broader spectrum of light, although filters are typically used to limit the range of emitted light to the preferred range mentioned above.

One reason it is useful for the QTH bulb to emit a broad spectrum of light is because many dental compounds cure at different wavelengths. For example, camphorquinone is a common photo-initiator that is most responsive to light having a wavelength of about 460 nm to about 470 nm. Other light-curable products, however, including many adhesives are cured when they are irradiated by light wavelengths in the 350 nm to 400 nm range. Accordingly, QTH bulbs can be used to cure both camphorquinone initiated products as well as adhesives.

One problem with QTH bulbs, however, is that they generate a relatively high quantity of heat, making it impractical to place QTH bulbs on the portions of the light-curing devices that are inserted within the mouth of a patient. In particular, if the QTH bulbs were disposed at the tips of the light-curing devices, the heat generated by the QTH bulbs could burn or agitate the sensitive mouth tissues of the patient. Accordingly, the QTH bulbs are typically disposed remotely from the portion of the light-curing device that is inserted within a patient's mouth. The heat generated by QTH bulbs also represents wasted energy, which increases the power requirement to achieve a desired light intensity.

To channel and direct the light emitted by a QTH bulb to the desired location within a patient's mouth, existing curing lights must utilize light guides, such as fiber optic wands and tubular light guides, or special reflectors. Although fiber optic wands and reflectors are useful for their intended purposes, they are somewhat undesirable because they can add to the cost and weight of the equipment, thereby increasing the overall cost and difficulty of performing the light-curing dental procedures.

In an attempt to overcome the aforementioned problems, some light-generating devices have been manufactured using alternative light generating sources, such as light-emitting diodes (LEDs) which are generally configured to only radiate light at specific wavelengths, thereby eliminating the need for special filters and generally reducing the amount of input power required to generate a desired output of radiation.

LEDs are particularly suitable light sources because they generate much less heat than QTH bulbs, thereby enabling the LEDs to be placed at the tip of the curing lights and to be inserted directly within the patient's mouth. This is particularly useful for reducing or eliminating the need for light guides such as optical fiber wands.

One limitation of LEDs, however, is that they are only configured to emit a narrow spectrum of light. For example, a 460 nm LED or LED array will generally only emit light having a spectrum of 460 nm±30 nm. Accordingly, a light curing device utilizing a 460 nm LED light source will be well designed to cure camphorquinone initiated products, but will not be suitable for curing adhesives that are responsive to light in the 400 nm±30 nm range. Likewise, a light-curing device utilizing a 400 nm light source may be suitable to cure some adhesives, but will be unsuitable for curing camphorquinone initiated products.

In an attempt to overcome this limited utility, some light generating devices have been manufactured that include multiple LEDs configured to emit light at different wavelengths. However, because the different wavelengths of light are generated at different points (in contrast to a QTH bulb, or light redirected through a light guide, for example), it can be difficult to produce sufficient intensities of desired wavelengths across the full footprint of light emitted by the device. In other words, there are often "hot" and "cold" areas within the footprint of light generated with respect to any given wavelength.

In view of the foregoing, there exists a need to develop dental curing lights including multiple LEDs capable of providing more even intensities of any given wavelength across the full footprint of light emitted. It would be a further improvement to provide a dental curing light capable of better blending different wavelengths across the full footprint of light emitted in order to provide a broader spectrum of light across the full footprint.

SUMMARY OF THE INVENTION

The present invention is directed to a dental curing light including an elongate wand having a proximal end and a distal end, a plurality of LEDs disposed at or near a distal end of the elongate wand and a printed circuit board for mounting the plurality of LEDs. The LEDs include a main through mount LED and a plurality of surface mount LEDs positioned around the main through mount LED. The main LED is through mounted relative to the printed circuit board such that the power connections of the main through mount LED are made through a hole or holes in the printed circuit board. The power connections of the main through mount LED are made on an opposite surface of the printed circuit board relative to the "top" surface to which the surface mount LEDs are mounted.

In one embodiment the main through mount LED is configured to emit light having a first peak wavelength. The plurality of surface mount LEDs may be configured to emit light having a second peak wavelength different from the first peak wavelength. One presently preferred embodiment includes a main through mount LED configured to emit light having a first peak wavelength (e.g., blue) while the plurality of surface mount LEDs are configured to emit light having a second peak wavelength different from the first peak wavelength (e.g., UV). According to one such implementation, light emitted by the main through mount LED and the plurality of surface mount LEDs is emitted so as to form substantially complete overlapping of footprints of first and second peak wavelengths within about eight millimeters of the plurality of LEDs, preferably within about three millimeters of the plurality of LEDs, and more preferably within about one millimeter of the plurality of LEDs.

The main through mount LED may emit light having a dispersion angle of at least about 120 degrees. The plurality of surface mount LEDs may individually emit light having a dispersion angle of at least about 70 degrees, preferably at least about 80 degrees, and more preferably at least about 90 degrees.

In one such embodiment the combined spectrum of first and second peak wavelengths is suitable for curing both camphorquinone initiated photosensitive products and photosensitive adhesives where the photosensitive adhesives have different photo curing requirements than the camphorquinone initiated photosensitive products (e.g., cured by UV wavelengths). In one specific implementation, the plurality of surface mount LEDs may also include one or more LEDs configured to emit light of at least a third peak wavelength.

The dental curing light may further include controls disposed upon the elongate wand for selectively controlling operation of the plurality of LEDs. According to one such embodiment, the controls may allow a user to separately and/or simultaneously activate the main through mount LED and/or the plurality of surface mount LEDs, as desired.

The plurality of surface mount LEDs may be positioned symmetrically around the main through mount LED. Through lensing and/or the geometry of placement, the main through mount LED and the plurality of surface mount LEDs may provide a footprint of any desired shape (e.g., round, elliptical, or other shape).

In one case, the printed circuit board may comprise one of a metal core printed circuit board, a metal backed printed circuit board, a metal core printed circuit board with a ceramic layer, a metal core printed circuit board having multiple metal core layers, or a printed circuit board having a core comprising a material having a high thermal conductivity (e.g., diamond, carbon, or silicon carbide).

The printed circuit board may alternatively comprise a flexible printed circuit board mounted to a thermally conductive substrate (e.g., copper, aluminum, magnesium, or carbon fiber). According to one such embodiment, the flexible printed circuit board may also comprise a thermally conductive material.

In one configuration, the main LED may be through mounted so as to be flush against the same top surface of the printed circuit board as that to which the plurality of surface mount LEDs are surface mounted. Alternatively, the main through mount LED may be mounted through a hole in the printed circuit board as to be flush against an opposite surface of the printed circuit board relative to the top mounting surface of the printed circuit board on which the plurality of the surface mount LEDs are mounted. In either case, the power connections for the main through mount LED are made on the opposite or so called "bottom" surface of the printed circuit board. Either of these arrangements provides substantially even intensities of one or more desired peak wavelengths across the full footprint of light emitted by the device. Furthermore, in the case of a device capable of emitting two or more peak wavelengths, better blending of the different wavelengths across the full footprint is provided so as to prevent "hot" and "cold" spots within the footprint.

These and other benefits, advantages and features of the present invention will become more full apparent from the following description and appended claims, or may be learned by the practice of the invention as set forth hereinafter.

BRIEF DESCRIPTION OF THE DRAWINGS

In order that the manner in which the above recited and other benefits, advantages and features of the invention are obtained, a more particular description of the invention briefly described above will be rendered by reference to specific embodiments thereof which are illustrated in the appended drawings. Understanding that these drawings depict only typical embodiments of the invention and are not therefore to be considered limiting of its scope, the invention will be described and explained with additional specificity and detail through the use of the accompanying drawings in which:

FIG. 2 illustrates an exemplary dental curing light of the invention that includes a plurality of LEDs disposed at the distal end of the elongate wand of the dental curing light;

FIGS. 3A and 3B illustrate close up top and side views respectively of one arrangement of a plurality of LEDs on a printed circuit board;

FIGS. 4A and 4B illustrate close up top and side views respectively of another arrangement of a plurality of LEDs on a printed circuit board;

DETAILED DESCRIPTION OF THE PREFERRED EMBODIMENTS

I. Introduction and Definitions

A detailed description of the invention will now be provided with specific reference to Figures illustrating various exemplary embodiments. It will be appreciated that like structures will be provided with like reference designations.

To help clarify the scope of the invention, certain terms will now be defined. The terms "LED" and "LED light source," as used herein, generally refer to one or more LEDs, one or more LED arrays, or any combination of the above that is capable of generating radiant energy that can be used to cure light curable compounds. The light emitted by an LED light source includes a limited spectrum of wavelengths with a peak wavelength that corresponds with the rating of the LED light source.

The present invention is directed to a dental curing light including an elongate wand having a proximal end and a distal end, a plurality of LEDs disposed at or near a distal end of the elongate wand and a printed circuit board for mounting the plurality of LEDs. The LEDs include a main through mount LED and a plurality of surface mount LEDs positioned around the main through mount LED. The main LED is through mounted relative to the printed circuit board such that the power connections of the main through mount LED are made through a hole or holes in the printed circuit board, such that the power connections are made on an opposite surface of the printed circuit board relative to the "top" surface to which the surface mount LEDs are mounted.

Figure 1:
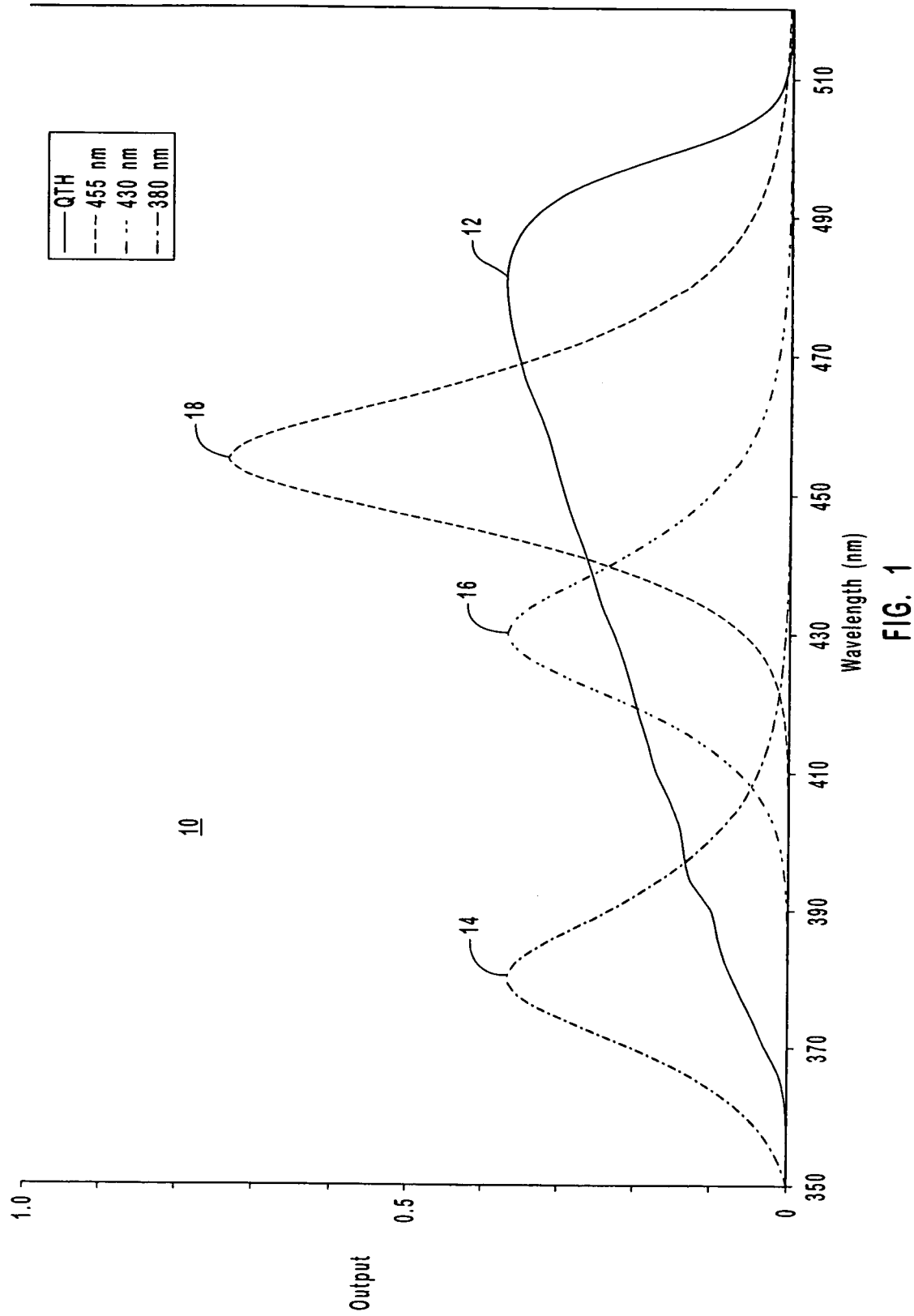
FIG. 1 illustrates a graph charting the spectral irradiance of a Quartz Tungsten Halogen (QTH) bulb, a 380 nm LED, a 430 nm LED, and a 455 nm LED.

FIG. 1 illustrates a graph 10 that charts the spectral irradiance or light spectra emitted from by a quartz-tungsten-halogen (QTH) bulb, a 380 nm LED light source, a 430 nm LED light source, and a 455 LED light source. The values given in the y-axis are generic such that no specific representation as to the actual power output should be assumed.

As shown in FIG. 1, the QTH spectrum 12 ranges from about 360 nm to about 510 nm. The 380 nm LED spectrum 14 ranges from about 350 nm to about 430 nm, with the most intense output of light being within the range of about 360 nm to about 400 nm. The 430 nm LED spectrum 16 ranges from about 390 nm to about 480 nm, with the most intense output of light being within the range of about 410 nm to about 450 nm. The 455 nm LED spectrum ranges from about 410 nm to about 510 nm, with the most intense output of light being within the range of about 430 nm to about 490 nm.

Also shown, each of the individual LED spectra 14, 16 and 18 individually comprise only a portion of the spectral range of wavelengths emitted by QTH spectrum 12. Accordingly, the utility of the LED spectra 14, 16, 18 is somewhat more specialized or limited than the spectral irradiance of the QTH spectrum 12. In particular, the QTH spectrum 12 can be used to cure adhesives that are responsive to light at about 370–390 nm (i.e., UV light), as well as camphorquinone initiated products that are responsive to light at about 455 nm (i.e., blue light). In contrast, none of the individual LED Spectra 14, 16 or 18 can be used to cure both camphorquinone initiated products with 455 nm light as well as adhesives with 370–390 nm light.

Accordingly, QTH bulbs have greater utility than individual LEDs from the standpoint of providing light in a broad spectrum. However, as mentioned above, the heat generated by QTH bulbs is undesirable and effectively prevents the QTH bulb from being placed on the portion of the light-curing device that is inserted within a patient's mouth, thereby requiring QTH bulb devices to be used with light-guides to direct the light to the desired location within a patient's mouth. In contrast, LED light sources can be placed at or near the ends of the light-curing devices and inserted within a patient's mouth. LEDs, however, emit only a narrow spectrum of light, effectively limiting their use to photo-curing a limited range of products, as compared to the broader range of products, that can be cured using a QTH bulb.

Accordingly, the curing lights of the present invention can be configured with a plurality of different types of LED light sources, as described below, to generate a composite and broad spectrum of light that is broader than a spectrum of light provided by any single LED light source. As further described below, the LED light sources can be arranged and configured to emit light in overlapping footprints.

II. An Exemplary Dental Curing Light

FIG. 2 illustrates an exemplary curing light 100. Dental curing light 100 includes an elongate wand 102 having a proximal end 104 and a distal end 106. Dental curing light 100 also includes a plurality of LEDs 108 and 110 disposed at or near the distal end 106 of elongate wand 102. The plurality of LEDs includes a main through mount LED 110 and a plurality of surface mount LEDs 108 positioned around main through mount LED 110. Dental curing light 100 also includes a printed circuit board 112 for mounting the plurality of LEDs. Perhaps as best seen in FIGS. 3A and 3B, main LED 110 is through mounted relative to printed circuit board 112 such that power connections 114 of the main through mount LED 110 are made through a hole or holes (not shown) formed through printed circuit board 112.

The dental curing light 100 may include controls disposed on elongate wand 102 for selectively controlling operation of main through mount LED 110 and plurality of surface mount LEDs 108. The controls may comprise any suitable control system. The illustrated embodiment includes multiple buttons 118 disposed on elongate wand 102. Buttons 118 or other control system may allow either separate or simultaneous activation of main LED 110 and/or surface mount LEDs 108, as desired.

FIGS. 3A and 3B illustrate close up top and side views, respectively, of printed circuit board 112 and the arrangement of LEDs 108 and 110 within dental curing light 100. As seen in these Figures, the larger main through mount LED 110 is positioned centrally and mounted in a through mount configuration such that power connections 114 are made on the reverse (i.e., opposite) surface of printed circuit board 112. A plurality of relatively smaller surface mount LEDs 108 are mounted and positioned around main LED 110. The illustrated embodiment includes 12 surface mounted LEDs 108 although fewer or more could alternatively be used. The combination of a through mounted main LED 110 and a plurality of surface mounted LEDs 108 positioned around the main LED 110 allows for many LEDs to be mounted in the small available space while also providing a geometric arrangement of LEDs that is capable of providing substantially even intensities of one or more desired peak wavelengths across the full footprint of light emitted by the device 100.

Furthermore, in the case of a device capable of emitting two or more peak wavelengths, better blending of the different wavelengths across the full combined footprint is provided so as to prevent "hot" and "cold" spots within the combined footprint. In other words, substantially complete overlapping of footprints (e.g., the footprint of light generated and emitted by main LED 110 and the footprint of light generated and emitted by the surface mount LEDs 108) of light emitted may be accomplished, resulting in prevention or minimization of "hot" or "cold" spots within both the individual footprints and the combined footprint.

FIGS. 4A and 4B illustrate close up top and side views, respectively, of an alternative embodiment of device 100' including printed circuit board 112', a main through mount LED 110', and a plurality of surface mount LEDs 108. Printed circuit board 112' includes a relatively large through mounting hole (not shown). This hole is sufficiently large so as to allow main LED 110' to be partially inserted through the bottom of the hole and to allow the power connections 114' of main LED 110' to be connected to pads on the opposite, "bottom" surface of printed circuit board 112'. Such an arrangement provides that main through mount LED 110' is mounted through a hole in the printed circuit board 112' so as to be flush against the opposite surface of printed circuit board 112' relative to the "top" mounting surface of printed circuit board 112' to which the plurality of surface mount LEDs 108 are mounted.

Because the surface mount LEDs 108 are mounted flush against the "top" surface of the printed circuit board 112', and the main through mount LED 110' is mounted flush against the opposite surface of printed circuit board 112', it may be desirable to select the thickness of the printed circuit board such that the plurality of surface mount LEDs 108 and the main through mount LED 110' are in substantially the same plane.

In addition, the relatively large hole formed through printed circuit board 112' may include a reflective surface on the inside surface of the hole to gather and redirect as much emitted light as possible. It may also be desirable to flare the sides of the hole for this same purpose.

Figure 5A:
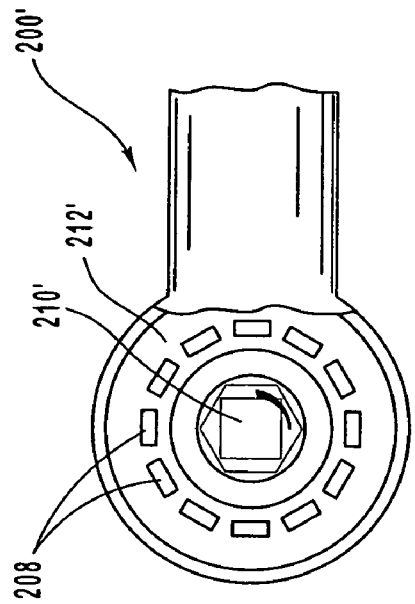
FIGS. 5A and 5B illustrate close up top and side views respectively of another arrangement of a plurality of LEDs on a printed circuit board.
Figure 5B:
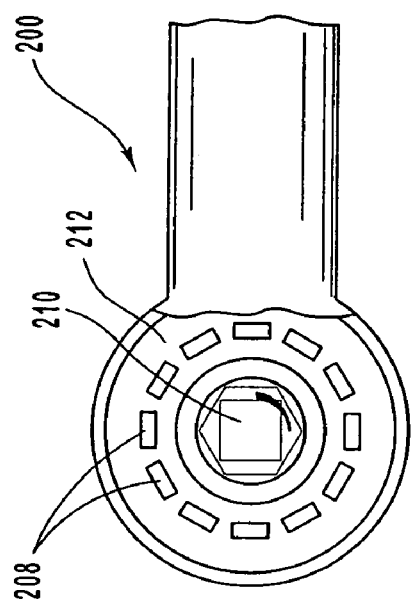

FIGS. 5A and 5B illustrate another alternative embodiment of device 200 including a printed circuit board 212, a main through mount LED 210, and a plurality of surface mount LEDs 208. As perhaps best seen in FIG. 5B, the power connections 214 of main LED 210 are connected to the bottom surface of printed circuit board 212 through small holes (not shown).

Figure 6A:
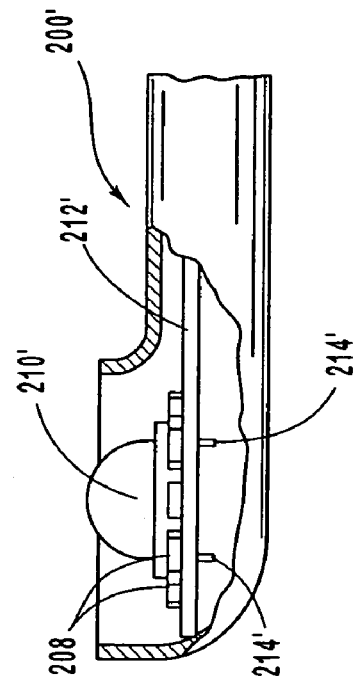
FIGS. 6A and 6B illustrate close up top and side views respectively of another arrangement of a plurality of LEDs on a printed circuit board.
Figure 6B:
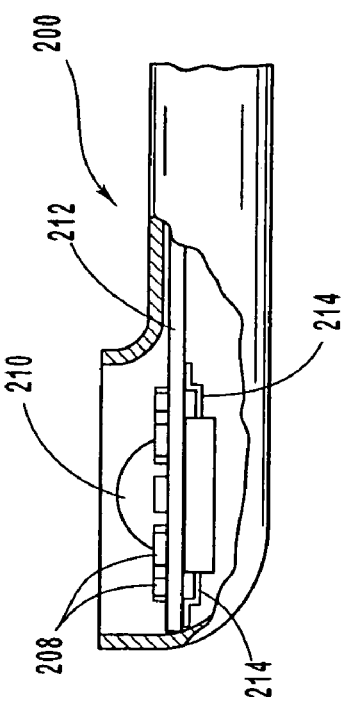

FIGS. 6A and 6B illustrate close up top and side views, respectively, of an alternative embodiment including printed circuit board 212', a main through mount LED 210', and a plurality of surface mount LEDs 208. Printed circuit board 212' includes a relatively large through mounting hole (not shown). This hole is sufficiently large so as to allow main LED 210' to be inserted through the bottom of the hole and to allow the power connections 214' of main LED 210 to be connected to pads on the opposite, "bottom" surface of printed circuit board 212'. Such an arrangement provides that main through mount LED 210' is mounted through the hole in the printed circuit board 212' so as to be flush against the opposite surface of printed circuit board 212' relative to the "top" mounting surface of printed circuit board 212' to which the plurality of surface mount LEDs 208 are mounted.

Because the surface mount LEDs 208 are mounted flush against the "top" surface of the printed circuit board 212', and the main through mount LED 210' is mounted flush against the opposite surface of printed circuit board 212', it may be desirable to select the thickness of the printed circuit board such that the plurality of surface mount LEDs 208 and the main through mount LED 210' are in substantially the same plane.

In addition, the relatively large hole formed through printed circuit board 212' may include a reflective surface on the inside surface of the hole to gather and redirect as much emitted light as possible. It may also be desirable to flare the sides of the hole for this same purpose.

The dental curing lights according to the invention may emit light in any desired footprint. The embodiments described in connection with FIGS. 3A and 3B, and 4A and 4B may produce elliptical footprints while the embodiments described in conjunction with FIGS. 5A and 5B, and 6A and 6B may describe embodiments of a dental curing light which may emit light having a round footprint. Although elliptical and round footprints have been disclosed, it is to be understood that the emitted footprint may be of any desired shape.

According to one embodiment, the main through mount LED (e.g., 110, 110', 210, or 210') may be configured to emit light having a first peak length (e.g., blue) while the plurality of surface mount LEDs 108 may be configured to emit light having a second peak wavelength (e.g., UV) different from the first peak wavelength. In some embodiments, some of the surface mount LEDs 108 may be configured to emit a second peak wavelength while other of the surface mount LEDs 108 are configured to emit a third peak wavelength.

Exemplary peak wavelengths for "blue" LED light sources may include, but are not limited to, 405 nm, 410 nm, 430 nm, 450 nm, 455 nm, 460 nm or 465 nm. Suitable exemplary LEDs are sold by Lumileds Lighting, LLC located in San Jose, Calif. Lumileds' 1, 3, and 5 watt LEDs are one currently preferred "blue" LED light source.

Exemplary peak wavelengths for "UV" LED light sources may include, but are not limited to 350 nm, 370 nm, 375 nm, 380 nm, 385 nm, 393 nm, 395 nm or 400 nm. Suitable exemplary LEDs are sold by Kingbright Corporation USA located in City of Industry, Calif. Kingbright's 1.3 watt LEDs are one currently preferred "UV" LED light source. If desired, any or all of the plurality of LEDs may be overdriven.

In one embodiment the through mount LED (e.g., 110, 110', 210, or 210') emits light having dispersion angle of at least about 120 degrees while the plurality of surface mount LEDs 108 may individually emit light having a dispersion angle of at least about 70 degrees, preferably at least about 80 degrees, and more preferably at least about 90 degrees.

The printed circuit board (e.g., 112, 112', 212, or 212') may comprise any suitable printed circuit board. Exemplary printed circuit boards include a metal core printed circuit board, a metal backed printed circuit board, a metal core printed circuit board with a ceramic layer, a metal core printed circuit board having multiple metal core layers or a printed circuit board having a core comprising a material having a high thermal conductivity (e.g., diamond, carbon, or silicon carbide). The printed circuit board may alternatively comprise a flexible printed circuit board mounted to a thermally conductive substrate. Examples of such substrates include, but are not limited to one or more of copper, aluminum, magnesium, or carbon fiber. If desired, a flexible printed circuit board may also comprise a thermally conductive material.

Figure 7A:
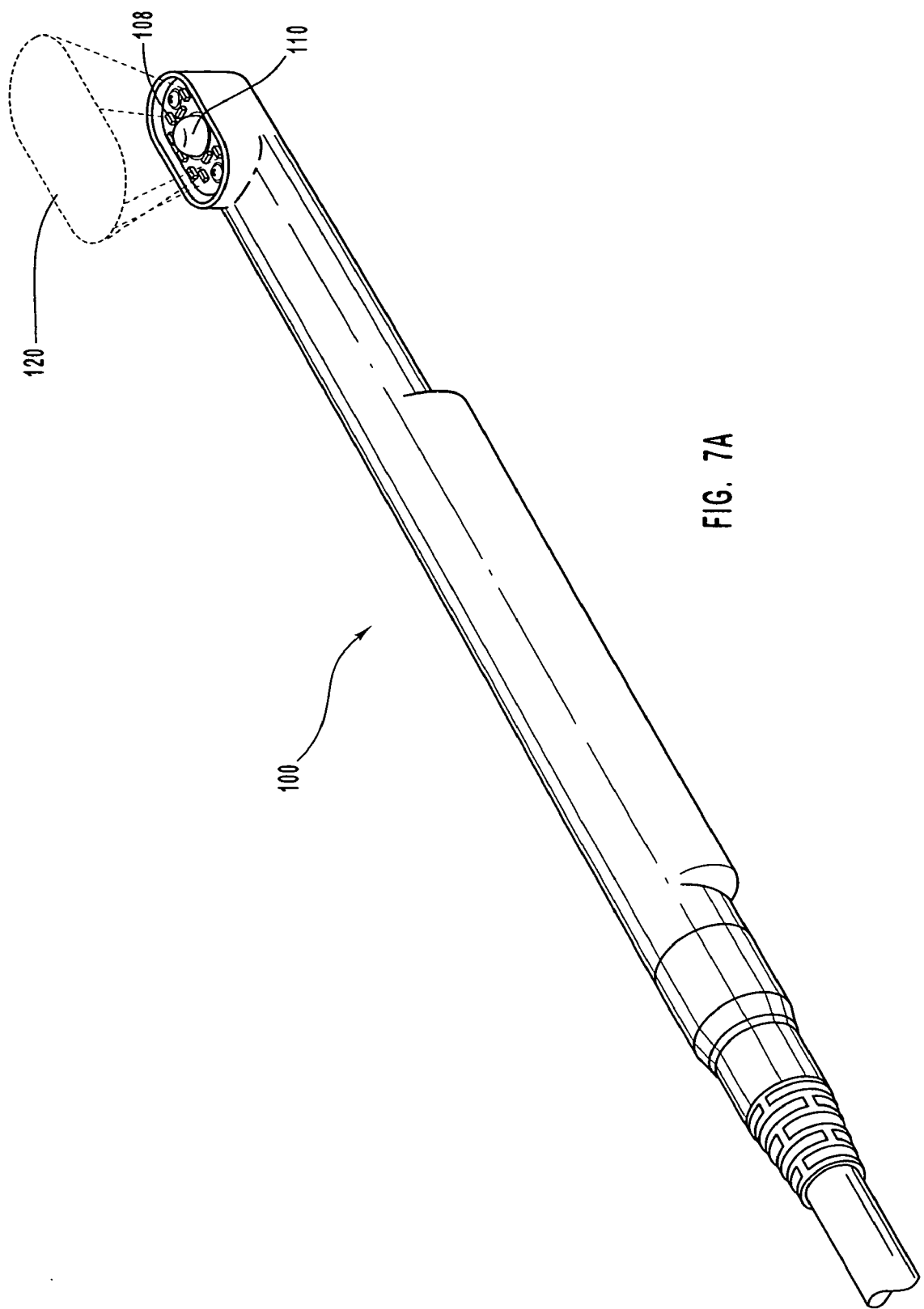
FIG. 7A illustrates an exemplary dental curing light including the arrangement of LEDs of FIGS. 3A and 3B, and also including a representation of emitted light forming an elliptical footprint.

FIG. 7A illustrates an exemplary elliptical footprint 120 emitted by dental curing light 100. It is to be understood that the footprints of light generated from main LED 110 and LEDs 108 are emitted so as to form complete overlapping of footprints at some distance from the plurality of LEDs. In the case where main LED 110 emits light having a first peak wavelength and LEDs 108 emit light having a second peak wavelength, it is preferred that substantially complete overlapping of footprints of first and second peak wavelengths occurs within about 8 mm of the plurality of LEDs, more preferably within about 3 mm of the plurality of LEDs, and most preferably within about 1 mm of the plurality of LEDs.

Figure 7B:
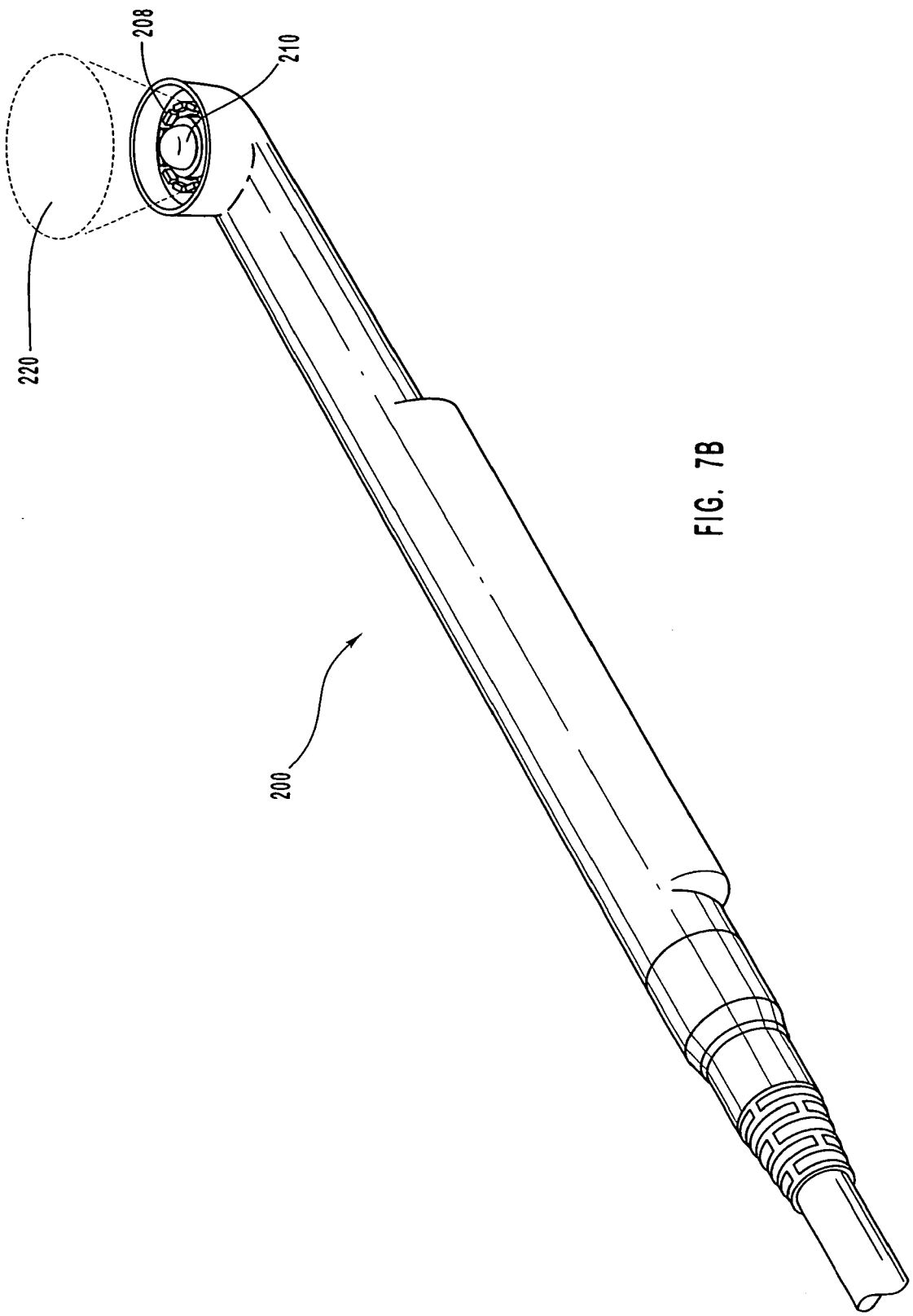
FIG. 7B illustrates an alternative exemplary dental curing light including the arrangement of LEDs of FIGS. 5A and 5B, and also including a representation of emitted light forming a round footprint.

FIG. 7B illustrates an exemplary elliptical footprint 220 emitted by dental curing light 200. It is to be understood that the footprints of light generated from main LED 210 and LEDs 208 are emitted so as to form complete overlapping of footprints at some distance from the plurality of LEDs. In the case where main LED 210 emits light having a first peak wavelength and LEDs 208 emit light having a second peak wavelength, it is preferred that substantially complete overlapping of footprints of first and second peak wavelengths occurs within about 8 mm of the plurality of LEDs, more preferably within about 3 mm of the plurality of LEDs, and most preferably within about 1 mm of the plurality of LEDs.

Because substantially complete overlapping of footprints of light emitted from the various LEDs occurs within such a short distance, the user is able to take advantage of a blended light output which may include first, second or more peak wavelengths for curing composite materials. Such a combined spectrum of first and second peak wavelengths is especially suitable for curing both camphorquinone initiated photosensitive products and photosensitive adhesives wherein the photosensitive adhesives have different photo curing requirements than the camphorquinone initiated photosensitive products.

It will be appreciated that the present claimed invention may be embodied in other specific forms without departing from its spirit or essential characteristics. The described embodiments are to be considered in all respects only as illustrative, not restrictive. The scope of the invention is, therefore, indicated by the appended claims rather than by the foregoing description. All changes that come within the meaning and range of equivalency of the claims are to be embraced within their scope.

What is claimed is:

1. A dental curing light comprising:
   an elongate wand having a proximal end and a distal end;
   a plurality of LEDs disposed at or near a distal end of the elongate wand,
      the LEDs including a larger main through mount LED and a plurality of smaller surface mount LEDs positioned to the side of or around the larger main through mount LED; and
   a printed circuit board for mounting the plurality of LEDs;
      wherein the surface mount LEDs are positioned on a top mounting surface of the printed circuit board and wherein the main through mount LED is through mounted relative to the printed circuit board such that power connections of the main through mount LED are disposed on or adjacent to a bottom surface of the printed circuit board opposite the top mounting surface.

2. A dental curing light as recited in claim 1, wherein the main through mount LED is configured to emit light having a first peak wavelength.

3. A dental curing light as recited in claim 2, wherein the main through mount LED is configured to emit light having a peak wavelength selected from 405 nm, 410 nm, 430 nm, 450 nm, 455 nm, 460 nm, or 465 nm.

4. A dental curing light as recited in claim 2, wherein the plurality of surface mount LEDs are configured to emit light having a second peak wavelength different from the first peak wavelength.

5. A dental curing light as recited in claim 4, wherein the plurality of surface mount LEDs are configured to emit light having a peak wavelength selected from 350 nm, 370 nm, 375 nm, 380 nm, 385 nm, 393 nm, 395 nm, or 400 nm.

6. A dental curing light as recited in claim 4, wherein the light emitted by the main through mount LED and the plurality of surface mount LEDs is emitted so as to form substantially complete overlapping of footprints of first and second peak wavelengths within about 8 mm of the plurality of LEDs.

7. A dental curing light as recited in claim 4, wherein the light emitted by the main through mount LED and the plurality of surface mount LEDs is emitted so as to form substantially complete overlapping of footprints of first and second peak wavelengths within about 3 mm of the plurality of LEDs.

8. A dental curing light as recited in claim 4, wherein the light emitted by the main through mount LED and the plurality of surface mount LEDs is emitted so as to form substantially complete overlapping of footprints of first and second peak wavelengths within about 1 mm of the plurality of LEDs.

9. A dental curing light as recited in claim 4, wherein the main through mount LED emits light having a dispersion angle of at least about 120°.

10. A dental curing light as recited in claim 4, wherein the plurality of surface mount LEDs individually emit light having a dispersion angle of at least about 70°.

11. A dental curing light as recited in claim 4, wherein the plurality of surface mount LEDs individually emit light having a dispersion angle of at least about 80°.

12. A dental curing light as recited in claim 4, wherein the plurality of surface mount LEDs individually emit light having a dispersion angle of at least about 90°.

13. A dental curing light as recited in claim 4, wherein the combined spectrum of first and second peak wavelengths is suitable for curing both camphorquinone initiated photosensitive products and photo-sensitive adhesives, wherein the photo-sensitive adhesives have different photo-curing requirements than the camphorquinone initiated photo-sensitive products.

14. A dental curing light as recited in claim 4, wherein the plurality of surface mount LEDs includes one or more LEDs configured to emit light of at least a third peak wavelength.

15. A dental curing light as recited in claim 1, wherein the plurality of LEDs are disposed on the elongate wand of the dental curing light in such a manner as to enable the plurality of LEDs to emit the first and second peak wavelengths of light to a desired treatment area within a patient's mouth without the use of a light-guide.

16. A dental curing light as recited in claim 1, further comprising controls disposed upon the elongate wand for selectively controlling operation of the main through mount LED and the plurality of surface mount LEDs, such that the main through mount LED and plurality of surface mount LEDs can be activated either separately or simultaneously, as desired.

17. A dental curing light as recited in claim 1, wherein the plurality of surface mount LEDs are positioned symmetrically around the main through mount LED.

18. A dental curing light as recited in claim 1, the printed circuit board comprising one of a metal core printed circuit board, a metal backed printed circuit board, a metal core printed circuit board with a ceramic layer, a metal core printed circuit board having multiple metal core layers, or a printed circuit board having a core comprising a material having a high thermal conductivity.

19. A dental curing light as recited in claim 18, the printed circuit board having a core comprising a material having a high thermal conductivity comprising one of diamond, carbon, or silicon carbide.

20. A dental curing light as recited in claim 1, the printed circuit board comprising a flexible printed circuit board mounted to a thermally conductive substrate.

21. A dental curing light as recited in claim 20, the thermally conductive substrate comprising one or more of copper, aluminum, magnesium, or carbon fiber.

22. A dental curing light as recited in claim 20, the flexible printed circuit board also comprising a thermally conductive material.

23. A dental curing light as recited in claim 1, wherein the main LED is mounted flush against the same surface of the printed circuit board as that to which the plurality of surface mount LEDs are surface mounted.

24. A dental curing light as recited in claim 1, wherein the main through mount LED is mounted through a hole in the printed circuit board so as to abut the bottom surface of the printed circuit board.

25. A dental curing light comprising:

an elongate wand having a proximal end and a distal end;

a plurality of LEDs disposed at or near a distal end of the elongate wand; and a printed circuit board for mounting the plurality of LEDs;

the plurality of LEDs including:

a larger main LED through mounted relative to the printed circuit board such that power connections of the main through mount LED are on or adjacent to a bottom surface of the printed circuit board, the through mounted main LED being configured to emit light having a first peak wavelength; and a plurality of smaller surface mount LEDs on a mounting surface of the printed circuit board opposite to the bottom surface, the surface mount LEDs being positioned symmetrically around the main through mount LED, the surface mount LEDs being configured to emit light having a second peak wavelength;

wherein the larger main through mount LED emits light having a dispersion angle of at least about 120°, and the plurality of smaller surface mount LEDs individually emit light having a dispersion angle of at least about 90°, such that the light emitted by the main through mount LED and the plurality of surface mount LEDs is emitted so as to form substantially complete overlapping of footprints of first and second peak wavelengths within about 1 mm of the plurality of LEDs.

26. A dental curing light comprising:

an elongate wand having a proximal end and a distal end;

a plurality of LEDs disposed at or near a distal end of the elongate wand;

the LEDs including a larger main through mount LED and a plurality of smaller surface mount LEDs positioned to the side of or around the main through mount LED; and a printed circuit board for mounting the plurality of LEDs;

wherein the surface mount LEDs are positioned on a top mounting surface of the printed circuit board and wherein the larger main through mount LED is mounted through a hole in the printed circuit board so as to be flush against bottom surface of the printed circuit board opposite the top mounting surface, wherein power connections of the main through mount LED are disposed on or adjacent to the bottom surface of the printed circuit board.

27. A dental curing light as recited in claim 26, wherein the thickness of the printed circuit board is such that the plurality of surface mount LEDs and the main through mount LED are in substantially the same plane.

28. A dental curing light as recited in claim 26, wherein the hole within the printed circuit board for through mounting the main LED includes a reflective surface on the inside surface of the hole.

29. A dental curing light as recited in claim 26, wherein the sides of the hole are flared.

* * * * *

UNITED STATES PATENT AND TRADEMARK OFFICE
CERTIFICATE OF CORRECTION

PATENT NO. : 7,210,814 B2 Page 1 of 1
APPLICATION NO. : 11/118147
DATED : May 1, 2007
INVENTOR(S) : Scott et al.

It is certified that error appears in the above-identified patent and that said Letters Patent is hereby corrected as shown below:

Title Page
Item 56, references cited, insert --6,719,559  4/04  Cao.............................483/29--

Column 4
Line 2, change "full" to --fully--

Column 5
Line 28, after "spectrum" insert --18--
Line 59, change "products," to --products--

Signed and Sealed this

Twenty-second Day of July, 2008

JON W. DUDAS
*Director of the United States Patent and Trademark Office*